(12) United States Patent
Bergmann et al.

(10) Patent No.: US 10,718,783 B2
(45) Date of Patent: Jul. 21, 2020

(54) DIAGNOSIS AND RISK STRATIFICATION OF INFECTIONS AND CHRONIC DISEASES OF THE RESPIRATORY TRACT AND LUNGS BY MEANS OF PROVASOPRESSIN, PARTICULARLY COPEPTIN OR NEUROPHYSIN II

(71) Applicant: BRAHMS GmbH, Henningsdorf (DE)

(72) Inventors: Andreas Bergmann, Berlin (DE); Nils Morgenthaler, Berlin (DE); Jana Papassotiriou, Berlin (DE); Joachim Struck, Berlin (DE); Beat Muller, Basel (CH)

(73) Assignee: BRAHMS GmbH, Henningsdorf (DE)

( * ) Notice: Subject to any disclaimer, the term of this patent is extended or adjusted under 35 U.S.C. 154(b) by 0 days.

(21) Appl. No.: 15/180,797

(22) Filed: Jun. 13, 2016

(65) Prior Publication Data
US 2017/0059583 A1 Mar. 2, 2017

Related U.S. Application Data

(63) Continuation of application No. 13/425,928, filed on Mar. 21, 2012, now abandoned, which is a continuation of application No. 12/514,524, filed as application No. PCT/DE2007/002037 on Nov. 11, 2007, now Pat. No. 8,158,368.

(30) Foreign Application Priority Data

Nov. 12, 2006 (DE) ........................ 10 2006 053 442

(51) Int. Cl.
*G01N 31/00* (2006.01)
*G01N 33/53* (2006.01)
*G01N 33/68* (2006.01)

(52) U.S. Cl.
CPC ... *G01N 33/6884* (2013.01); *G01N 2800/122* (2013.01); *G01N 2800/50* (2013.01); *G01N 2800/52* (2013.01); *G01N 2800/60* (2013.01)

(58) Field of Classification Search
CPC ..... G01N 2333/575; G01N 2333/5754; G01N 2333/5757; G01N 2800/325
See application file for complete search history.

(56) References Cited

U.S. PATENT DOCUMENTS

| | | | |
|---|---|---|---|
| 6,562,946 B2 | 5/2003 | Althaus et al. | |
| 6,756,483 B1 | 6/2004 | Bergmann et al. | |
| 7,498,139 B2 | 3/2009 | Bergmann et al. | |
| 8,188,368 B2 * | 5/2012 | Suzuki | B60R 16/0215 |
| | | | 174/101 |
| 9,229,013 B2 * | 1/2016 | Bergmann | G01N 33/74 |
| 9,261,516 B2 * | 2/2016 | Bergmann | G01N 33/74 |
| 2009/0098571 A1 | 4/2009 | Bergmann et al. | |
| 2010/0173321 A1 | 7/2010 | Hamm et al. | |

FOREIGN PATENT DOCUMENTS

| | | | | |
|---|---|---|---|---|
| DE | 10027954 A1 | 6/2001 | | |
| EP | 0656121 B1 | 3/1998 | | |
| EP | 1121600 B1 | 8/2001 | | |
| WO | 004/006860 A1 | 1/2004 | | |
| WO | 2006/018315 A1 | 2/2006 | | |
| WO | WO2006018315 A1 * | 2/2006 | ............. | G01N 33/74 |
| WO | WO-2006018315 A1 * | 2/2006 | ............. | G01N 33/74 |

OTHER PUBLICATIONS

Morganthaler et al. (Clinical Chemistry, 52(10, 112-119, 2006, publisher on-line Nov. 2005).*
Tascilar et al. (Annals of Oncology 10,Suppl. 4:S107-S110, 1999).*
Tockman et al. (Cancer Research 52:2711s-2718s, 1992).*
Pullan et al., J. Clin. Endocrin & Metabol., 49:580-587, 1979.
Morganthaler et al., Clinical Chemistry, 52(1): 112-119, 2006; published on-line Nov. 2005.
Legros, J.J., et al., "Neurophysins as Markers of Vasopressin and Oxytocin Release", Horm. Res., vol. 34, pp. 151-155, (1990).
North, W.G., "Clinical Evaluation of the Neurophysins as Tumor Markers in Small Cell Lung Cancer", Recent Results in Cancer Research, vol. 99, pp. 187-193, (1985).
North, W.G., "Human Neurophysins as Potential Tumor Markers for Small Cell Carcinoma of the Lung: Application of Specific Radioimmunoassays", Journal of Clinical Endocrinology and Metabolism, vol. 51, No. 4, pp. 892-896, (1980).
Seligman et al., Decreases in procalcitonin and C-reactive protein are strong predictors of survival in ventilator-associated pneumonia:, Critical Care, vol. 10, No. 5, pp. 1-9, 2006.
Stolz et al., "Diagnostic Value of Signs, Symptoms and Laboratory Values in Lower Respiratory Tract Infection", Swiss Med Wkly, vol. 138, pp. 434-440, 2006.
Stolz et al., Copeptin, C-Reactive Protein, and Procalcitonin as Prognostic Biomarkers in Acute Exacerbation of COPD:, Chest, vol. 131, pp. 1058-1067, 2007.

* cited by examiner

*Primary Examiner* — Lisa V Cook
(74) *Attorney, Agent, or Firm* — Millen White Zelano and Branigan, PC; John Sopp

(57) ABSTRACT

A method for diagnosing and/or stratifying the risk of infections or chronic diseases of the respiratory tract and lungs, particularly lower respiratory tract infections and chronic obstructive pulmonary disease, in which method provasopressin (proAVP) or fragments or partial peptides thereof, especially copeptin or neurophysin II, is/are determined. Suitable biomarker combinations for in-vitro diagnosis are also included.

7 Claims, 3 Drawing Sheets
Specification includes a Sequence Listing.

Amino acid sequence pre-provasopressin:

```
MPDTMLPACF LGLLAFSSAC YFQNCPRGGK PAMSDLELRQ CLPCGPGGKG RCFGPSICCA    60
DELGCFVGTA EALRCQEENY LPSPCQSGQK ACGSGGRCAA FGVCCNDESC VTEPECREGF   120
HRRARASDRS NATQLDGPAG ALLLRLVQLA GAPEPFEPAQ PDAY                    164
```

1-19        Signal sequence 20-28 ARG-VASOPRESSIN 32-124     NEURPHYSIN II 126-164    COPEPTIN

Fig. 1

DIAGNOSIS AND RISK STRATIFICATION OF INFECTIONS AND CHRONIC DISEASES OF THE RESPIRATORY TRACT AND LUNGS BY MEANS OF PROVASOPRESSIN, PARTICULARLY COPEPTIN OR NEUROPHYSIN II

The invention relates to a method for diagnosis and/or risk stratification of infections or chronic diseases of the airways and lungs, particularly of lower respiratory tract infections (LRTI) and COPD (chronic obstructive pulmonary disease), where a determination of provasopressin (proAVP) or fragments and partial peptides thereof, particularly copeptin or neurophysin II, is carried out. Furthermore, the invention relates to a combination of biomarkers for in vitro diagnosis, suitable for this purpose.

For the purpose of suitable therapy, an early diagnosis and differentiation of the infections or chronic diseases of the airways and lungs is/are already required in the emergency room, in connection with the need to make clinical decisions. Because of the non-specific symptoms (difficulty breathing) in the case of infections or chronic diseases of the airways and lungs, both differentiation and a distinction from other diseases, and recognition of the concrete infection or chronic disease of the airways and lungs, are essential.

Copeptin (also: C-terminal proAVP) is described in WO 2006/018315 (BRAHMS AG) as a biomarker for in vitro diagnosis of heart disease and related pulmonary dysfunctions ("pulmonary disorders"). A copeptin assay related to this is disclosed in Morgenthaler et al. (Nils G. Morgenthaler, Joachim Struck, Christine Alonso and Andreas Bergmann, Assay for the Measurement of Copeptin, a Stable Peptide Derived from the Precursor of Vasopressin, Clinical Chemistry 52: 112-119, 2006).

In the state of the art, the procalcitonin (PCT) determination is described for the purpose of a study to distinguish bacterial sepsis (threshold value >0.5 ng/mL) from other disease causes (EP0656121). PCT is also described in the literature in connection with pneumonias, where the studies are primarily related, with regard to a diagnosis, to discriminating between different pathogen types in the case of pneumonia that has already been diagnosed (Prat C, Dominguez J, Andreo F, Blanco S, Pallares A, Cuchillo F, Ramil C, Ruiz-Manzano J, Ausina V, Procalcitonin and neopterin correlation with aetiology and severity of pneumonia, J Infect. 52(3) (2006): pp 169-177 and Masia M, Gutierrez F, Shum C, Padilla S, Navarro J C, Flores E, Hernandez I, Masia M, Gutierrez F, Shum C, Padilla S, Navarro J C, Flores E, Hernandez I {sic—repetition of names in original}, Chest 128(4) (2005): pp 2223-2239, Boussekey N, Leroy O, Georges H, Devos P, d'Escrivan T, Guery B, Diagnostic and prognostic values of admission procalcitonin levels in community-acquired pneumonia in an intensive care unit. Infection 33(4) (2005): pp 257-63). In a study by Zhou et al (Zhou C D et al Zhongguo Wei Zhong Bing Ji Jiu Yi Xue. 2006 June, 18(6), 370-2), PCT is presented as a diagnostic marker for early diagnosis of ventilator-associated pneumonia in an intensive care unit. PCT is also described as a diagnostic marker in pneumonias (Prat et al. 2006 (supra) and Masia M et al. 2005 (supra), Boussekey N et al. 2005 (supra), Christ-Crain M, Morgenthaler N G, Solz D, Muller C, Bingisser R, Harbarth S, Tamm M, Struck J, Bergmann A, Muller B, Pro-adrenomedullin to predict severity and outcome in community-acquired pneumonia, Crit Care 10(3) (2006): pp R96). Furthermore, there are studies in which it was shown that clinically relevant infections (including bacterial pneumonias) that require antibiotic therapy are detected in patients who are suspected of having infections of the lower airways (including pneumonia), using PCT, at a threshold concentration of >0.1 ng/mL and >0.25 ng/mL, respectively (Christ-Crain M, Stolz D, Bingisser R, Muller C, Miedinger D, Huber P R, Zimmerli W, Harbarth S, Tamm M, Muller B, Procalcitonin Guidance of Antibiotic Therapy in Community-acquired Pneumonia: A Randomized Trial, Am J Respir Crit Care Med 174(1) (2006), pp. 84-93 and Christ-Crain M, Jaccard-Stolz D, Bingisser R, Gencay M M, Huber P R, Tamm M, Muller B, Effect of procalcitonin-guided treatment on antibiotic use and outcome in lower respiratory tract infections: cluster-randomized, single-blinded intervention trial, Lancet 21; 363(9409) (2004): pp 600-607, Stolz D, Christ-Crain M, Gencay M M, Bingisser R, Huber P R, Muller B, Tamm M, Diagnostic value of signs, symptoms and laboratory values in lower respiratory tract infection, Swiss Med Wkly 8; 136(27-28) (2006): pp 434-440).

However, a marker combination of copeptin and procalcitonin is not described.

Certain clinical studies concerning COPD are known (Soler-Cataluna J J, Martinez-Garcia M A, Roman Sanchez P, et al. Severe acute exacerbations and mortality in patients with chronic obstructive pulmonary disease. Thorax 1005; 60:925-931; Antonelli Incalzi R, Fuso L, De Rosa M, et al. Co-morbidity contributes to predict mortality of patients with chronic obstructive pulmonary disease. Eur Respir J 1997; 10:2794-2800; Yohannes A M, Baldwin R C, Connolly M J. Predictors of 1-year mortality in patients discharged from hospital following acute exacerbation of chronic obstructive pulmonary disease. Age Ageing 2005; 34:491-496; Almagro P, Barreiro B, Ochoa de Echaguen A, et al. Risk factors for hospital readmission in patients with chronic obstructive pulmonary disease. Respiration 2006; 73:311-317).

However, it is a disadvantage of known diagnosis methods using previously known markers that early and complete detection of risk patients is not successful, and therefore risk stratification takes place only to an insufficient degree. One task that underlies the invention therefore consists in developing a method for risk stratification for diagnosis and/or risk stratification of infections or chronic diseases of the airways and lungs, which allows an improved detection of at-risk patients. {sic—first occurrence of "for risk stratification in preceding sentence appears to be superfluous}

It is furthermore disadvantageous that in the state of the art, sufficient sensitivity and/or specificity of the markers is generally not achieved.

Another task therefore consists in making available a method for diagnosis and/or risk stratification of infections or chronic diseases of the airways and lungs, where at least one marker or a combination of markers demonstrates sufficient sensitivity and specificity.

It is therefore the task of the present invention to make available a method for diagnosis and/or risk stratification of infections or chronic diseases of the airways and lungs.

This task is accomplished by means of a method for diagnosis and/or risk stratification of infections or chronic diseases of the airways and lungs, where a determination of provasopressin (proAVP) or fragments and partial peptides thereof, particularly copeptin or neurophysin II, is carried out (hereinafter: method according to the invention).

Surprisingly, provasopressins (proAVPs) or fragments and partial peptides thereof, preferably copeptin or neurophysin II, demonstrate great sensitivity and specificity for the diagnosis of infections or chronic diseases of the airways and lungs.

Within the scope of this invention, the term "infections of the airways and lungs" is particularly understood to mean those infections that are caused by bacteria, viruses, fungi, or parasites, for example those indications such as lower respiratory tract infections (LRTI), bronchitis, pneumonia, sarcoidosis, bronchiectases, non-cardiac pulmonary edema.

Furthermore, lower respiratory tract infections (LRTI), bronchitis, putrid bronchitis, pneumonia are particularly preferred, according to the invention.

Pneumonia, particularly community associated pneumonia (CAP), and lower respiratory tract infections (LRTI) are very particularly preferred.

Within the scope of this invention, pneumonia is understood to mean an acute or chronic disease of the lung tissue, and its infection is caused by bacteria, viruses or fungi, parasites, rarely also toxically by means of inhalation of toxic substances, or immunologically. For the clinician, pneumonia is a constellation of various symptoms (fever or hypothermia, shivers, cough, pleuritic thorax pain, increased sputum production, increased respiratory rate, dull percussion sound, bronchial breathing, crepitation close to the ear, pleural rubbing) in combination with at least one infiltrate that can be seen on the thorax X-ray (Harrisons Innere Medizin {Harrison's Internal Medicine}, published by Manfred Dietel, Norbert Suttorp and Martin Zeitz, ABW Wissenschaftsverlag 2005).

Within the scope of this invention, "chronic diseases of the lungs and airways" are understood to be those indications such as interstitial lung diseases and lung fibroses, chronic obstructive pulmonary diseases (COPD), particularly COPD infection exacerbations, bronchial asthma, particularly infection exacerbations in cases of bronchial asthma, bronchial carcinoma. COPD, particularly COPD infection exacerbations, is/are particularly preferred.

According to the invention, COPD refers to a group of chronic diseases that are characterized by coughing, increased sputum, and difficulty breathing when under stress. Chronic-obstructive bronchitis and pulmonary emphysema should primarily be mentioned. Both disease profiles are characterized in that exhalation (expiration) is particularly hindered. A colloquial term for the main symptom of COPD is also "smoker's cough." The invention is particularly advantageous in cases of acute exacerbations.

According to the invention, the term "risk stratification" comprises finding those patients, particularly emergency patients and at-risk patients, who have a poorer prognosis, for the purpose of more intensive diagnosis and therapy/ treatment of infections or chronic diseases of the airways and lungs, with the goal of allowing the most advantageous possible course. Risk stratification according to the invention therefore allows an effective treatment method, which are possible in the case of infections or chronic diseases of the airways and lungs, using medications, particularly antibiotics. {sic—singular direct object in first part of sentence, plural verb in relative clause relating to this direct object}

For this reason, the invention also relates to identification of patients having an increased risk and/or a disadvantageous prognosis of infections or chronic diseases of the airways and lungs, specifically in the case of symptomatic and/or asymptomatic patients, particularly emergency patients.

In the case of emergency and/or intensive-care medicine, in particular, reliable stratification can take place by means of the method according to the invention, in particularly advantageous manner. The method according to the invention therefore allows clinical decisions that lead to rapid therapy success and to the avoidance of deaths. Such a clinical decision, according to the invention, also comprises hospitalization of the patients.

For this reason, the invention also relates to a method for diagnosis and/or risk stratification of infections or chronic diseases of the airways and lungs, for the purpose of making clinical decisions, such as further treatment and therapy by means of medications, particularly antibiotics, preferably in the time-critical situation of intensive-care medicine or emergency medicine.

In another preferred embodiment, the method according to the invention therefore relates to therapy control of an infection or chronic disease of the airways and lungs.

In another preferred embodiment of the method according to the invention, the diagnosis and/or risk stratification takes place for prognosis, for early recognition and recognition by means of a differential diagnosis, for an assessment of the degree of severity, and for an assessment of the progression over the course of therapy.

In another preferred embodiment, the invention relates to a method for in vitro diagnosis and/or risk stratification of infections or chronic diseases of the airways and lungs, where a determination of the marker provasopressin (proAVP) or fragments and partial peptides thereof, particularly copeptin or neurophysin II, is carried out on a patient to be examined. However, copeptin or a fragment or partial sequence thereof is particularly preferred. In particular, copeptin demonstrates an advantageously great stability in the serum and plasma, for purposes of in vitro diagnosis (Morgenthaler N G, Struck J, Alonso C., et al. Assay for the measurement of copeptin, a stable peptide derived from the precursor of vasopressin, Clin Chem 2006; 52:112-119).

Furthermore, the invention relates a method for diagnosis and/or risk stratification of infections and chronic diseases of the airways and lungs, or to a method for in vitro diagnosis for early or differential diagnosis or prognosis of infections or chronic diseases of the airways and lungs, according to one of the above embodiments, where after occurrence of the symptoms, a cut-off (threshold value) range of 6-20 pmol/L of the marker provasopressin (proAVP) or fragments and partial peptides thereof, particularly copeptin or neurophysin II, is significant (specific) for diagnosis and/or risk stratification. Furthermore, a cut-off (threshold value) of 6-10 pmol/L, particularly 9 pmol/L, is preferred, preferably 2 hours after occurrence of the symptoms.

Furthermore, the invention relates to a method for diagnosis and/or risk stratification of infections or chronic diseases of the airways and lungs, or to a method for early or differential diagnosis or prognosis of infections or chronic diseases of the airways and lungs, according to one of the above embodiments, where after occurrence of the symptoms, a cut-off (threshold value) of 10-50 pmol/L of the marker provasopressin (proAVP) or fragments and partial peptides thereof, particularly copeptin or neurophysin II, is significant (specific) for prognosis and/or risk stratification. Furthermore, a cut-off (threshold value) of 10-40 pmol/L is preferred.

On this basis, these methods according to the invention are advantageously sensitive.

In an embodiment of the method according to the invention, bodily fluid, particularly blood, is taken from the patient to be examined, optionally whole blood or serum or obtainable plasma, and the diagnosis takes place in vitro/ex vivo, i.e. outside of the human or animal body. On the basis of the determination of the marker provasopressin (proAVP)

or fragments and partial peptides thereof, particularly copeptin and neurophysin II, great sensitivity and specificity for infections or chronic diseases of the airways and lungs are achieved, and the diagnosis or risk stratification can take place using the amount that is present in at least one patient sample. However, the marker copeptin (stable fragment of proAVP or pre-provasopressin) or a fragment or partial sequence thereof is particularly preferred.

Within the scope of this invention, "provasopressin" is understood to be a human protein or polypeptide that can be obtained from pre-provasopressin (SEQ ID NO:3), and comprises the amino acids 29-164 within the scope of pre-provasopressin (see also WO2006/018315 and FIG. 1), and fragments or partial peptides that can be obtained from it, particularly copeptin (fragment: amino acids 126-164 (39 amino acids: SEQ ID NO:1: ASDRSNATQL DGPAGALLLR LVQLAGAPEP FEPAQPDAY) or neurophysin II (fragment: amino acids 32-124 of pre-provasopressin (93 amino acids: SEQ ID NO:2: AMSDLELRQC LPCGPGGKGR CFGPSICCAD ELGCFVGTAE ALRCQEENYL PSPCQSGQKA CGSGGRCAAF GVCCNDESCV TEPECREGFH RRA). Furthermore, these polypeptides according to the invention can demonstrate post-translational modifications, such as glycolization, lip(o)idization, or derivativization.

In another embodiment, the determination of provasopressin (proAVP) or fragments and partial peptides thereof, particularly copeptin or neurophysin II, can additionally take place with further markers, specifically preferably those that already indicate infections or chronic diseases of the airways and lungs.

For this reason, the invention relates to an embodiment of the method according to the invention where the determination is additionally carried out with at least one further marker selected from the group of inflammatory markers, in a patient to be examined.

According to the invention, the inflammatory marker can be selected from at least one marker of the group of C-reactive protein (CRP), cytokines, such as TNF-alpha, for example, interleukins, such as IL-6, for example, procalcitonin (1-116, 3-116), and adhesion molecules, such as VCAM or ICAM.

In a particularly preferred embodiment, the invention relates to a particularly advantageous combination of biomarkers, specifically provasopressin (proAVP) or fragments and partial peptides thereof, particularly copeptin or neurophysin II, with procalcitonin (1-116, 3-116) and/or the group of C-reactive protein (CRP).

For this reason, the invention relates to a method for in vitro diagnosis and/or risk stratification of infections or chronic diseases of the airways and lungs, where a determination of the marker provasopressin (proAVP) or fragments and partial peptides thereof, particularly copeptin or neurophysin II, is carried out, in combination with procalcitonin (1-116, 3-116) or a partial sequence thereof, in each instance, in a patient to be examined. Again, a combination of neurophysin II, copeptin and procalcitonin is particularly preferred, particularly copeptin and procalcitonin. These stated biomarker combinations demonstrate synergies, in particularly advantageous manner, which lead to improved specificity and sensitivity for diagnosis of the {word/words missing}.

Within the scope of this invention, "procalcitonin" is understood to be a human protein or polypeptide having an amino acid sequence of 1-116 amino acids or 2-116 amino acids (PCT 2-116) or 3-116 amino acids (PCT 3-116), as described in EP0656121, EP1121600 of the applicant, as well as DE10027954A1. Furthermore, the procalcitonin according to the invention can demonstrate post-translational modifications, such as glycolization, lip(o)idization, or derivativization. Furthermore, partial sequences or fragments of procalcitonin are also included.

In another embodiment of the invention, the method according to the invention can be carried out within the scope of an in vitro diagnosis, by means of parallel or simultaneous determination of the markers (e.g. multi-titer plates with 96 cavities and more), where the determinations are carried out on at least one patient sample.

Furthermore, the method according to the invention and its determinations can be carried out using an automated analysis device, particularly using a Kryptor (www.kryptor.net).

In another embodiment, the method according to the invention and its determinations can be carried out by means of a rapid test (e.g. lateral flow test), whether using single-parameter or multi-parameter determinations. In a particularly preferred embodiment, this is a self-test or a device that is suitable for use in emergency diagnosis.

Furthermore, the invention relates to the use of provasopressin (proAVP) or fragments and partial peptides thereof, particularly copeptin or neurophysin II, for diagnosis and/or risk stratification of infections or chronic diseases of the airways and lungs, and/or for in vitro diagnosis for early or differential diagnosis or prognosis of infections or chronic diseases of the airways and lungs.

In a particular embodiment, the invention relates to the use of provasopressin (proAVP) or fragments and partial peptides thereof, particularly copeptin or neurophysin II, in combination with procalcitonin (1-116, 3-116) or a partial sequence thereof, in each instance, for diagnosis and/or risk stratification of infections or chronic diseases of the airways and lungs.

Use according to the invention can take place with at least one other suitable marker, if necessary (called "panel" or "cluster").

Another task is making available a corresponding diagnostic device for carrying out the method according to the invention.

Within the scope of this invention, such a diagnostic device is particularly understood to be an array or assay (e.g. immune assay, ELISA, etc.), in the broadest sense a device for carrying out the method according to the invention.

The invention furthermore relates to a kit for diagnosis and/or risk stratification of infections or chronic diseases of the airways and lungs, containing detection reagents for determining the provasopressin (proAVP) or fragments and partial peptides thereof, particularly copeptin or neurophysin II, and possibly additional markers mentioned above. Such detection reagents comprise antibodies, etc., for example.

The following examples and figures serve for a more detailed explanation of the invention, but without restricting the invention to these examples and figures.

EXAMPLES AND FIGURES

Example 1

Blood samples were taken of patients who came to the emergency room of a hospital with the leading symptom of respiratory distress, during the initial examination.

Number of test subjects: 167

Sample-Taking, Biomarker Analysis:

Blood samples were taken by means of standard serum Monovettes. After a coagulation period of 20-40 min, centrifugation was carried out for 15 min at 2000 g; subsequent serum separation was carried out by means of decanting. The serum samples were stored at −20 degrees C. until further use.

Copeptin assay according to Morgenthaler et al (Morgenthaler N G, Struck J, Alonso C, et al. Assay for the measurement of copeptin, a stable peptide derived from the precursor of vasopressin, Clin Chem 2006; 52:112-119).

Detection limit: 1.7 pmol/L.

COPD in the Case of Acute Worsening (Event):

It was possible to determine that copeptin, CRP, and procalcitonin were significantly increased after 14 days or 6 months.

Copeptin values of 167 patients (age (mean) 70 years) were studied. The patients came to the emergency room with acute exacerbation of an existing COPD. The patients were examined clinically with regard to their pulmonary function, at admission, after 14 days, and after 6 months. Table 1 shows an overview of the clinical parameters of the patients upon admission to the emergency room.

TABLE 1

Clinical parameters at admission of 167 patients with acute exacerbation of a COPD

| Parameter | n = 167 |
| --- | --- |
| Sex (M/F) (%) | 75/92 |
|  | (44.9/55.1) |
| Age in years (from to) | 70 (42-91) |
| Smoking packages/year | 45 (30-60) |
| {Translator's Note: The German word used, Packungen, translates literally to packages - unclear whether packs or cartons are meant} | |
| Average duration of COPD months (SD) | 127 (86) |
| Duration of exacerbation in days | 4 (3-7) |
| Cough (%) | 142 (85) |
| Increased sputum production (%) | 113 (67.7) |
| Discolored sputum (%) | 95 (56.9) |
| Difficulty breathing (%) | 155 (92.8) |
| Fever (%) | 68 (40.7) |
| Comorbidity (%) | |
| Cardiopathy | 76 (45.5) |
| Tumor | 24 (14.4) |
| Diabetes mellitus | 19 (11.4) |
| Severity of COPD - GOLD stage (%) | |
| I | 10 (6.0) |
| II | 35 (21.0) |
| III | 74 (44.3) |
| IV | 48 (28.7) |
| FEV1 in liters (SD) | 0.892 (0.397) |
| FEV1% expected (%) | 39.9 (16.9) |
| PaO$_2$ mmHg | 62.9 (15.7) |
| PaCO$_2$ mmHg | 43.8 (11.0) |
| Leukocytes × 10$^9$/l (SD) | 11.27 (4.7) |

In a multi-variant analysis (p=0.006, Cox Regression Analysis), the measured copeptin value was a predictor for a poor clinical progression, independent of age, existing comorbidity, hypoxemia, and restricted pulmonary function. It was only possible to achieve successful long-term therapy in 44 percent of the patients who had copeptin values ≥40 pmol/L upon admission. In contrast to this, it was possible to achieve success in 82 percent of the patients who had copeptin values <40 pmol/L (p<0.0001).

From this, it becomes evident that copeptin represents a prognosis marker for a disadvantageous clinical progression in the case of patients with COPE (and other pulmonary diseases). Copeptin could identify those patients who need particularly intensive therapy for their existing pulmonary diseases, at an early point in time.

Table 2 and FIGS. 2 and 3 explain the situation in detail.

TABLE 2

Comparison of the clinical result of patients with copeptin levels <40 pmol/L and ≥40 pmol/L upon admission

|  | Copeptin <40 pmol/L n = 140 | Copeptin ≥40 pmol/L n = 27 | p value |
| --- | --- | --- | --- |
| Hospitalization period <24 hours % (n) | 26.4% (37) | 3.7% (1) | 0.010 |
| Period of hospitalization Days (IQR) | 8.5 (1-15) | 14 (8-18) | 0.002 |
| Need for intensive-care unit % (n) | 6.4% (9) | 25.9% (7) | 0.002 |
| Period of intensive-care unit (IQR) | 2 (1.5-4.5) | 5 (3-5) | 0.097 |
| Hospitalization rate within 6 months | 0.17 ± 0.4 | 0.55 ± 0.74 | 0.005 |
| Average time to clinical failure | 163 ± 45 | 111 ± 73 | <<0.001 |
| Long-term clinical failure % (n) | 17.9% (25) | 55.6% (15) | <<0.001 |
| Death during hospitalization % (n) | 1.4% (2) | 11.1% (3) | 0.007 |
| Death within 6 months % (n) | 5% (7) | 25.9% (7) | <<0.001 |

BRIEF DESCRIPTION OF THE DRAWINGS

FIG. 1 shows the amino acid sequence (SEQ ID NO:3) of pre-provasopressin.

Number of patients on the days indicated (d):

Copeptin <40 pmol/L:

n=140 (0 d) 88 (5 d) 54 (10 d) 28 (15 d) 12 (20 d) 1 (25 d) 1 (30 d) 0 (35 d)

Copeptin ≥40 pmol/L:

n=27 (0 d) 23 (5 d) 18 (10 d) 12 (15 d) 5 (20 d) 4 (25 d) 1 (30 d) 0 (35 d)

Figure 2:
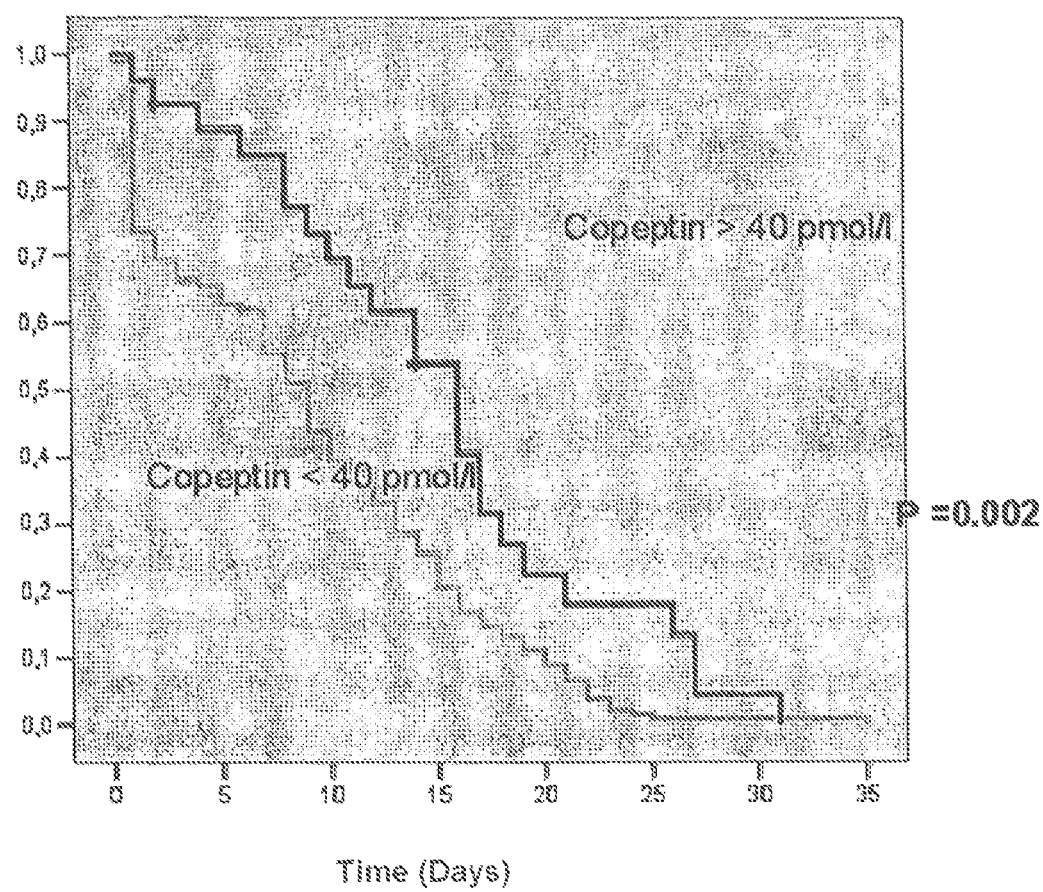
FIG. 2 shows the relationship between stays in the hospital of patients with CAP/pneumonia and the measured copeptin plasma value upon admission. This is shown as a probability of hospital discharge over time. Patients with copeptin values <40 pmol/L upon admission had a significantly shorter hospital stay in comparison with patients with copeptin values > 40 pmol/L.
Figure 3:
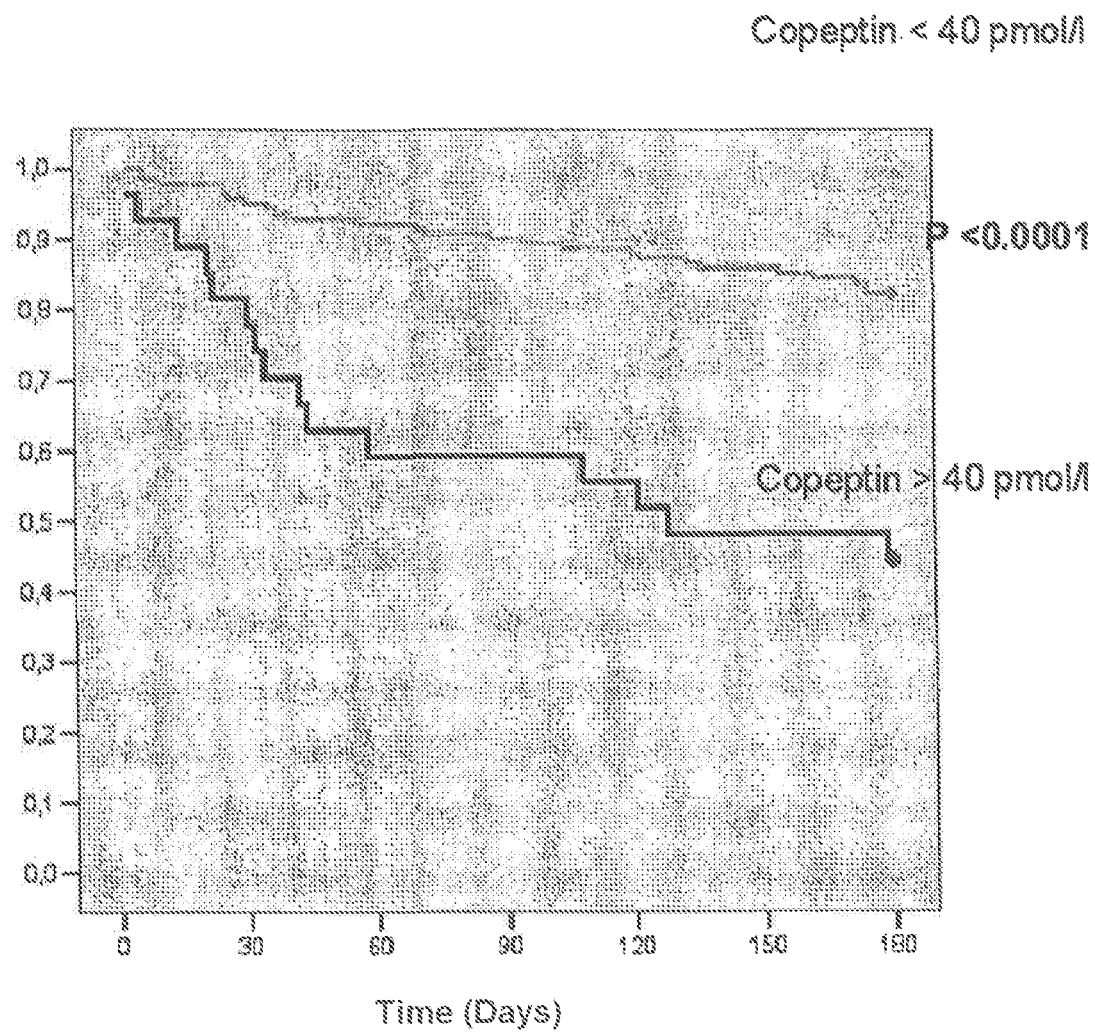

FIG. 3 shows the relationship between the frequency of complications (death, repeat hospitalization after discharge) and the copeptin plasma value upon admission. This is shown as the time free of event (freedom of event). Event is defined as death or repeat hospitalization after initial discharge. Patients with copeptin values <40 pmol/L upon admission had this event significantly less frequently than patients with copeptin values >40 pmol/L. Number of patients on the days indicated (d):

Copeptin <40 pmol/L:

n=140 (0 d) 133 (30 d) 129 (60 d) 126 (90 d) 123 (120 d) 120 (150 d) 115 (180 d)

Copeptin >40 pmol/L:

n=27 (0 d) 21 (30 d) 16 (60 d) 16 (90 d) 15 (120 d) 13 (150 d) 12 (180 d)

The invention claimed is:

1. A method for treating a patient having an infection or chronic disease of the airways and lungs and pneumonia, said method comprising:

a determination of copeptin in at least one sample of body fluid from the patient, wherein the patient has a presence in said sample of bodily fluid of more than 40 pmol/L of copeptin which identifies the patient needing intensive therapy for pneumonia, and treating the patient with antibiotics.

2. The method according to claim 1, comprising a determination of copeptin in combination with procalcitonin and/or C-reactive protein (CRP) in the sample of bodily fluid of the patient.

3. The method according to claim 1, further comprising a determination of at least one inflammatory marker in the sample of bodily fluid of the patient.

4. The method according to claim 3, wherein the inflammatory marker is at least one of TNF-alpha, IL-6, VCAM or ICAM.

5. The method according to claim 3, wherein simultaneous determinations of the copeptin and inflammatory markers are carried out.

6. The method according to claim 5, wherein determinations are carried out using an automated analysis device.

7. The method according to claim 5, wherein determinations are carried out by means of a rapid test.

\* \* \* \* \*

SEQUENCE LISTING

<160> NUMBER OF SEQ ID NOS: 3

<210> SEQ ID NO 1
<211> LENGTH: 39
<212> TYPE: PRT
<213> ORGANISM: Homo sapiens

<400> SEQUENCE: 1

Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
            20                  25                  30

Pro Ala Gln Pro Asp Ala Tyr
        35

<210> SEQ ID NO 2
<211> LENGTH: 93
<212> TYPE: PRT
<213> ORGANISM: Homo sapiens

<400> SEQUENCE: 2

Ala Met Ser Asp Leu Glu Leu Arg Gln Cys Leu Pro Cys Gly Pro Gly
1               5                   10                  15

Gly Lys Gly Arg Cys Phe Gly Pro Ser Ile Cys Cys Ala Asp Glu Leu
            20                  25                  30

Gly Cys Phe Val Gly Thr Ala Glu Ala Leu Arg Cys Gln Glu Glu Asn
        35                  40                  45

Tyr Leu Pro Ser Pro Cys Gln Ser Gly Gln Lys Ala Cys Gly Ser Gly
    50                  55                  60

Gly Arg Cys Ala Ala Phe Gly Val Cys Cys Asn Asp Glu Ser Cys Val
65                  70                  75                  80

Thr Glu Pro Glu Cys Arg Glu Gly Phe His Arg Arg Ala
                85                  90

<210> SEQ ID NO 3
<211> LENGTH: 164
<212> TYPE: PRT
<213> ORGANISM: Homo sapiens

<400> SEQUENCE: 3

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Pro Ala
            20                  25                  30

Met Ser Asp Leu Glu Leu Arg Gln Cys Leu Pro Cys Gly Pro Gly Gly
        35                  40                  45

Lys Gly Arg Cys Phe Gly Pro Ser Ile Cys Cys Ala Asp Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
        115                 120                 125

Arg Ser Asn Ala Thr Gln Leu Asp Gly Pro Ala Gly Ala Leu Leu Leu
    130                 135                 140

```
Arg Leu Val Gln Leu Ala Gly Ala Pro Glu Pro Phe Glu Pro Ala Gln
145                 150                 155                 160

Pro Asp Ala Tyr
```